(12) United States Patent
Kunikata et al.

(10) Patent No.: US 6,197,297 B1
(45) Date of Patent: *Mar. 6, 2001

(54) MONOCLONAL ANTIBODY SPECIFIC TO POLYPEPTIDE WHICH INDUCES INTERFERON-GAMMA PRODUCTION

(75) Inventors: Toshio Kunikata; Mutsuko Taniguchi; Keizo Kohno; Masashi Kurimoto, all of Okayama (JP)

(73) Assignee: Kabushiki Kaisha Hayashibara Seibutsu Kagaku Kenkyujo, Okayama (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/558,818

(22) Filed: Nov. 15, 1995

(30) Foreign Application Priority Data

Feb. 23, 1995 (JP) .................................... 7-058240

(51) Int. Cl.[7] .................. A61K 39/395; C12N 15/07; C07K 16/34
(52) U.S. Cl. ................. 424/156.1; 424/144.1; 424/142.1; 424/141.1; 424/130.1; 530/388.23; 530/388.85; 530/388.15; 530/387.1; 530/350; 530/344; 435/70.21; 435/70.1; 435/344.1; 435/326; 435/325; 435/366; 435/452; 435/451; 435/449; 514/12; 514/21
(58) Field of Search .................. 424/156.1, 144.1, 424/142.1, 141.1, 130.1; 530/388.23, 388.85, 388.15, 387.1, 350, 344; 435/70.21, 344.1, 326, 325, 366, 70.1, 452, 451, 449; 514/12, 21

(56) References Cited

PUBLICATIONS

Sevier et al, Clinical Chemistry, vol. 27(11), pp. 1797–1806, (1981).*

Goding, Journal of Immunological Methods, vol. 39, pp. 285–308, (1980).*

Okamura et al, Nature, vol. 378, pp. 88–91, (Nov. 2, 1995).*

Okamura et al, Infection and Immunity, vol. 63(10), pp. 3966–3972, (10/1995).*

Nakamura et al, Infection and Immunity, vol. 57(2), pp. 590–595, (2/1989).*

Nakamura et al, Infection and Immunity, vol. 61(1), pp. 64–70, (1/1993).*

Toyama, S. et al., Experimental Manual for Monoclonal Antibody, pp. v–153 (1987).

Tijssen, P. ed. "Enzyme Immunoassay." Laboratory Techniques in Biochemistry and Molecular Biology. pp. 196–197 (1989).

* cited by examiner

Primary Examiner—T. D. Wessendorf
(74) Attorney, Agent, or Firm—Browdy and Neimark (57) ABSTRACT

A monoclonal antibody which is specific to a polypeptide having a molecular weight of 18,500±3,000 daltons on SDS-PAGE and a pI of 4.9±1.0 on chromatofocusing. The monoclonal antibody is obtainable from hybridomas and can be used for the purification and detection of the polypeptide. The polypeptide strongly induces the IFN-γ production by immunocompetent cells with only a small amount, and does not cause serious side effects even when administered to human in a relatively-high dose.

6 Claims, 2 Drawing Sheets

| MOLECULAR WEIGHT (DALTONS) | MARKER | LANE 1 | LANE 2 |
|---|---|---|---|
| 67k |  | | |
| 45k |  | | |
| 30k |  | | |
| 20.1k |  | |  |
| 14.4k |  | | |

SEQUENCE LISTING (1) GENERAL INFORMATION:

(iii) NUMBER OF SEQUENCES:9

(2) INFORMATION FOR SEQ ID NO:1:

(i) SEQUENCE CHARACTERISTICS:
        (A) LENGTH:157 amino acids
        (B) TYPE:amino acid
        (D) TOPOLOGY:linear    (ii) MOLECULE TYPE:peptide    (xi) SEQUENCE DESCRIPTION:SEQ ID NO:1:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
20                  25                  30

Met Thr Asp Ser Asp Cys Arg Asp Asn Ala Pro Arg Thr Ile Phe Ile
35                  40                  45

Ile Ser Met Tyr Lys Asp Ser Gln Pro Arg Gly Met Ala Val Thr Ile
50                  55                  60

Ser Val Lys Cys Glu Lys Ile Ser Xaa Leu Ser Cys Glu Asn Lys Ile
65                  70                  75                  80

Ile Ser Phe Lys Glu Met Asn Pro Pro Asp Asn Ile Lys Asp Thr Lys
85                  90                  95

Ser Asp Ile Ile Phe Phe Gln Arg Ser Val Pro Gly His Asp Asn Lys
100                 105                 110

Met Gln Phe Glu Ser Ser Ser Tyr Glu Gly Tyr Phe Leu Ala Cys Glu
115                 120                 125

Lys Glu Arg Asp Leu Phe Lys Leu Ile Leu Lys Lys Glu Asp Glu Leu
130                 135                 140

Gly Asp Arg Ser Ile Met Phe Thr Val Gln Asn Glu Asp
145                 150                 155
```

(2) INFORMATION FOR SEQ ID NO:2:

(i) SEQUENCE CHARACTERISTICS:
        (A) LENGTH:471 base pairs
        (B) TYPE:nucleic acid
        (C) STRANDEDNESS:double
        (D) TOPOLOGY:linear    (ii) MOLECULE TYPE:cDNA to mRNA    (vi) ORIGINAL SOURCE:
        (A) ORGANISM:human
        (B) INDIVIDUAL ISOLATE:liver    (ix) FEATURE:
        (A) NAME/KEY:mat peptide
        (B) LOCATION:1..471
        (C) IDENTIFICATION METHOD:S    (xi) SEQUENCE DESCRIPTION:SEQ ID NO:2:

```
TAC TTT GGC AAG CTT GAA TCT AAA TTA TCA GTC ATA AGA AAT TTG AAT      48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT      96
Asp Gln Val Leu Phe Ile Asp Gln Gly Asn Arg Pro Leu Phe Glu Asp
20                  25                  30

ATG ACT GAT TCT GAC TGT AGA GAT AAT GCA CCC CGG ACC ATA TTT ATT     144
Met Thr Asp Ser Asp Cys Arg Asp Asn Ala Pro Arg Thr Ile Phe Ile
35                  40                  45

ATA AGT ATG TAT AAA GAT AGC CAG CCT AGA GGT ATG GCT GTA ACT ATC     192
Ile Ser Met Tyr Lys Asp Ser Gln Pro Arg Gly Met Ala Val Thr Ile
50                  55                  60
```

```
TCT GTG AAG TGT GAG AAA ATT TCA AYT CTC TCC TGT GAG AAC AAA ATT    240
Ser Val Lys Cys Glu Lys Ile Ser Xaa Leu Ser Cys Glu Asn Lys Ile
65              70                  75                  80

ATT TCC TTT AAG GAA ATG AAT CCT CCT GAT AAC ATC AAG GAT ACA AAA    288
Ile Ser Phe Lys Glu Met Asn Pro Pro Asp Asn Ile Lys Asp Thr Lys
85              90                  95

AGT GAC ATC ATA TTC TTT CAG AGA AGT GTC CCA GGA CAT GAT AAT AAG    336
Ser Asp Ile Ile Phe Phe Gln Arg Ser Val Pro Gly His Asp Asn Lys
100             105                 110

ATG CAA TTT GAA TCT TCA TCA TAC GAA GGA TAC TTT CTA GCT TGT GAA    384
Met Gln Phe Glu Ser Ser Ser Tyr Glu Gly Tyr Phe Leu Ala Cys Glu
115             120                 125

AAA GAG AGA GAC CTT TTT AAA CTC ATT TTG AAA AAA GAG GAT GAA TTG    432
Lys Glu Arg Asp Leu Phe Lys Leu Ile Leu Lys Lys Glu Asp Glu Leu
130             135                 140

GGG GAT AGA TCT ATA ATG TTC ACT GTT CAA AAC GAA GAC                471
Gly Asp Arg Ser Ile Met Phe Thr Val Gln Asn Glu Asp
145             150                 155
```

(2) INFORMATION FOR SEQ ID NO:3:

(i) SEQUENCE CHARACTERISTICS:
        (A) LENGTH:11
        (B) TYPE:amino acid
        (D) TOPOLOGY:linear     (ii) MOLECULE TYPE:peptide     (v) FRAGMENT TYPE:N-terminal fragment     (xi) SEQUENCE DESCRIPTION:SEQ ID NO:3:

```
Met Tyr Phe Gly Lys Leu Glu Ser Lys Leu Ser
1               5                   10
```

(2) INFORMATION FOR SEQ ID NO:4:

(i) SEQUENCE CHARACTERISTICS:
        (A) LENGTH:25
        (B) TYPE:amino acid
        (D) TOPOLOGY:linear     (ii) MOLECULE TYPE:peptide     (v) FRAGMENT TYPE:internal fragment     (xi) SEQUENCE DESCRIPTION:SEQ ID NO:4:

```
Ile Ile Ser Phe Glu Glu Met Asp Pro Pro Glu Asn Ile Asp Asp Ile
1               5                   10                  15

Gln Ser Asp Leu Ile Phe Phe Gln Lys
20                  25
```

(2) INFORMATION FOR SEQ ID NO:5:

(i) SEQUENCE CHARACTERISTICS:
        (A) LENGTH:18
        (B) TYPE:amino acid
        (D) TOPOLOGY:linear     (ii) MOLECULE TYPE:peptide     (v) FRAGMENT TYPE:internal fragment     (xi) SEQUENCE DESCRIPTION:SEQ ID NO:5:

```
Gln Pro Val Phe Glu Asp Met Thr Asp Ile Asp Gln Ser Ala Ser Glu
1               5                   10                  15

Pro Gln
```

(2) INFORMATION FOR SEQ ID NO:6:

(i) SEQUENCE CHARACTERISTICS:
        (A) LENGTH:471 base pairs
        (B) TYPE:nucleic acid
        (C) STRANDEDNESS:double
        (D) TOPOLOGY:linear     (ii) MOLECULE TYPE:cDNA to mRNA     (vi) ORIGINAL SOURCE:
        (A) ORGANISM:mouse
        (B) INDIVIDUAL ISOLATE:liver     (ix) FEATURE:
        (A) NAME/KEY:mat peptide
        (B) LOCATION:1..471
        (C) IDENTIFICATION METHOD:S     (xi) SEQUENCE DESCRIPTION:SEQ ID NO:6:

```
AAC TTT GGC CGA CTT CAC TGT ACA ACC GCA GTA ATA CGG AAT ATA AAT        48
Asn Phe Gly Arg Leu His Cys Thr Thr Ala Val Ile Arg Asn Ile Asn
1               5                  10                  15

GAC CAA GTT CTC TTC GTT GAC AAA AGA CAG CCT GTG TTC GAG GAT ATG        96
Asp Gln Val Leu Phe Val Asp Lys Arg Gln Pro Val Phe Glu Asp Met
20                  25                  30

ACT GAT ATT GAT CAA AGT GCC AGT GAA CCC CAG ACC AGA CTG ATA ATA       144
Thr Asp Ile Asp Gln Ser Ala Ser Glu Pro Gln Thr Arg Leu Ile Ile
35                  40                  45

TAC ATG TAC AAA GAC AGT GAA GTA AGA GGA CTG GCT GTG ACC CTC TCT       192
Tyr Met Tyr Lys Asp Ser Glu Val Arg Gly Leu Ala Val Thr Leu Ser
50                  55                  60

GTG AAG GAT AGT AAA AYG TCT ACC CTC TCC TGT AAG AAC AAG ATC ATT       240
Val Lys Asp Ser Lys Xaa Ser Thr Leu Ser Cys Lys Asn Lys Ile Ile
65                  70                  75                  80

TCC TTT GAG GAA ATG GAT CCA CCT GAA AAT ATT GAT GAT ATA CAA AGT       288
Ser Phe Glu Glu Met Asp Pro Pro Glu Asn Ile Asp Asp Ile Gln Ser
85                  90                  95

GAT CTC ATA TTC TTT CAG AAA CGT GTT CCA GGA CAC AAC AAG ATG GAG       336
Asp Leu Ile Phe Phe Gln Lys Arg Val Pro Gly His Asn Lys Met Glu
100                 105                 110

TTT GAA TCT TCA CTG TAT GAA GGA CAC TTT CTT GCT TGC CAA AAG GAA       384
Phe Glu Ser Ser Leu Tyr Glu Gly His Phe Leu Ala Cys Gln Lys Glu
115                 120                 125

GAT GAT GCT TTC AAA CTC ATT CTG AAA AAA AAG GAT GAA AAT GGG GAT       432
Asp Asp Ala Phe Lys Leu Ile Leu Lys Lys Lys Asp Glu Asn Gly Asp
130                 135                 140

AAA TCT GTA ATG TTC ACT CTC ACT AAC TTA CAT CAA AGT                   471
Lys Ser Val Met Phe Thr Leu Thr Asn Leu His Gln Ser
145                 150                 155
```

(2) INFORMATION FOR SEQ ID NO:7:

(i) SEQUENCE CHARACTERISTICS:
        (A) LENGTH:157 amino acids
        (B) TYPE:amino acid
        (D) TOPOLOGY:linear     (ii) MOLECULE TYPE:peptide     (vi) ORIGINAL SOURCE:
        (A) ORGANISM:mouse
        (B) INDIVIDUAL ISOLATE:liver     (xi) SEQUENCE DESCRIPTION:SEQ ID NO:7:

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
20              25                  30

Thr Asp Ile Asp Gln Ser Ala Ser Glu Pro Gln Thr Arg Leu Ile Ile
35              40                  45

Tyr Met Tyr Lys Asp Ser Glu Val Arg Gly Leu Ala Val Thr Leu Ser
50              55                  60

Val Lys Asp Ser Lys Xaa Ser Thr Leu Ser Cys Lys Asn Lys Ile Ile
65              70                  75                  80

Ser Phe Glu Glu Met Asp Pro Pro Glu Asn Ile Asp Asp Ile Gln Ser
85              90                  95

Asp Leu Ile Phe Phe Gln Lys Arg Val Pro Gly His Asn Lys Met Glu
100             105                 110

Phe Glu Ser Ser Leu Tyr Glu Gly His Phe Leu Ala Cys Gln Lys Glu
115             120                 125

Asp Asp Ala Phe Lys Leu Ile Leu Lys Lys Lys Asp Glu Asn Gly Asp
130             135                 140

Lys Ser Val Met Phe Thr Leu Thr Asn Leu His Gln Ser
145             150                 155
```

(2) INFORMATION FOR SEQ ID NO:8:

(i) SEQUENCE CHARACTERISTICS:
        (A) LENGTH:34 base pairs
        (B) TYPE:nucleic acid
        (C) STRANDEDNESS:double
        (D) TOPOLOGY:linear     (ii) MOLECULE TYPE:cDNA to mRNA     (xi) SEQUENCE DESCRIPTION:SEQ ID NO:8:

ATAGAATTCA AATGTACTTT GGCAAGCTTG AATC           34

(2) INFORMATION FOR SEQ ID NO:9:

(i) SEQUENCE CHARACTERISTICS:
        (A) LENGTH:27 base pairs
        (B) TYPE:nucleic acid
        (C) STRANDEDNESS:double
        (D) TOPOLOGY:linear     (ii) MOLECULE TYPE:cDNA to mRNA     (xi) SEQUENCE DESCRIPTION:SEQ ID NO:9:

ATAAAGCTTC TAGTCTTCGT TTTGAAC          27

US 6,197,297 B1

MONOCLONAL ANTIBODY SPECIFIC TO POLYPEPTIDE WHICH INDUCES INTERFERON-GAMMA PRODUCTION

BACKGROUND OF THE INVENTION

1. Field of the Invention

The present invention relates to a novel monoclonal antibody, more particularly, to a monoclonal antibody which is specific to a polypeptide capable of inducing the interferon-γ (hereinafter abbreviated as "IFN-γ") production by immunocompetent cells.

2. Description of the Prior Art

It is known that IFN-γ is a protein which has antiviral-, antioncotic- and immunoregulatory-activities, and is produced by immunocompetent cells stimulated with antigens or mitogens. Because of these biological activities, IFN-γ is expected to be used as an antitumor agent from the beginning of the finding, and is studied energetically on clinical trials as a therapeutic agent for malignant tumors in general including brain tumors. IFN-γ preparations now commercially available are roughly classified into 2 groups, i.e. natural IFN-γs produced by immunocompetent cells and recombinant IFN-γs produced by transformants obtained by introducing into microorganisms of the species *Escherichia coli* DNAs which encode such natural IFN-γs. In the above clinical trials, one of these IFN-γs is administered to patients as an "exogenous IFN-γ".

Among these IFN-γs, natural IFN-γs are usually produced by culturing established immunocompetent cells in nutrient culture media supplemented with IFN-γ inducers to form IFN-γs, and purifying the formed IFN-γs. It is known that the type of IFN-γ inducers greatly influence the IFN-γ yield, as well as the facility of IFN-γ purification and the safety of the final products. Generally, mitogens such as concanavalin A (Con A), *Lens culinaris, Phytolacca americana*, endotoxin and lipopolysaccharide are used as an IFN-γ inducer. However, these mitogens have problems related to their molecular varieties and quality changes depending on their origins and purification methods, as well as the difficulty of obtaining a desired amount of preparations with a constant IFN-γ inducibility. In addition, most of these mitogens induce unfavorable side effects when administered to living bodies, and some of them even cause toxicity, so that it is substantially difficult to induce the IFN-γ production by direct administrations to living bodies.

The present inventors found in mouse liver a substance which induces IFN-γ production during their research of cytokines produced from mammalian cells. They isolated the substance by using a variety of purification methods comprising column chromatography as a main technique, and studied the properties and features, revealing that the substance was a protein having the following physicochemical properties:

(1) Molecular weight
   Exhibiting a molecular weight of 19,000±5,000 daltons on sodium dodecyl polyacrylamide gel electrophoresis (SDS-PAGE);
(2) Isoelectric point (pI)
   Exhibiting an isoelectric point of 4.8±1.0 on chromatofocusing;
(3) Partial amino acid sequence
   Having the partial amino acid sequences in SEQ ID NOs:4 and 5; and
(4) Biological activity
   Inducing the IFN-γ production by immunocompetent cells.

It can be concluded that it is a novel substance because no protein with these physicochemical properties has been known. The present inventors continued studies on mouse liver cells and have found that the DNA (SEQ ID NO:6) of the substance consists of 471 base pairs and encodes the amino acid sequence in SEQ ID NO:7.

Based on these findings, the present inventors continued studies on human liver cells and have obtained a DNA which encodes another novel substance that induces IFN-γ production by immunocompetent cells. They revealed that the substance is a polypeptide and decoded its DNA and revealed that the polypeptide has the amino acid sequence in SEQ ID NO:1. They introduced the DNA into *Escherichia coli* to express the polypeptide and obtained the polypeptide in the resultant culture in a considerably high yield. These findings were disclosed in Japanese Patent Application Nos.184,162/94 and 304,203/94, applied for by the present inventors.

As is described above, the polypeptide has a property of inducing the IFN-γ production by immunocompetent cells, and is expected to be used in a variety of fields as an IFN-γ inducer, antiviral agent, antitumor agent, antibacterial agent, immunoregulatory agent, and blood platelet enhancing agent. In general, the developments of methods for efficiently purifying biologically active polypeptides to give a relatively-high purity and those for assaying many samples in parallel are inevitably required when the polypeptides should be incorporated into pharmaceuticals. Although the best material enabling these purification and assay is a monoclonal antibody, none of which specific to the polypeptide has been established.

SUMMARY OF THE INVENTION

In view of the foregoing, the object of the present invention is to provide a monoclonal antibody which is specific to the polypeptide.

It is another object of the present invention to provide a hybridoma capable of producing the monoclonal antibody.

It is further object of the present invention to provide a method for preparing the monoclonal antibody.

It is yet another object of the present invention to provide a purification method for purifying the polypeptide using the monoclonal antibody.

It is another object of the present invention to provide a detection method for assaying the polypeptide using the monoclonal antibody.

[Means to Attain the Object]

The first object of the present invention is attained by a monoclonal antibody which is specific to a polypeptide having either the amino acid sequence in SEQ ID NO:1 or a homologous amino acid sequence thereunto, and induces IFN-γ production by immunocompetent cells.

The second object of the present invention is attained by a hybridoma capable of producing the monoclonal antibody.

The third object of the present invention is attained by a process for preparing the monoclonal antibody comprising culturing the hybridoma capable of producing the antibody in vitro, i.e. in a nutrient culture medium, or in vivo, i.e. an animal, and collecting the antibody from the resultant culture or the body fluid.

The fourth object of the present invention is attained by a purification method for polypeptide comprising contacting the monoclonal antibody with a mixture containing the polypeptide and impurities to adsorb the polypeptide thereunto, and desorbing the polypeptide from the antibody.

The fifth object of the present invention is attained by a method for detecting the polypeptide comprising contacting samples with the monoclonal antibody to effect immunological reaction to detect the polypeptide.

BRIEF DESCRIPTION OF THE ACCOMPANYING DRAWINGS

KGFHH2 cDNA: cDNA encoding the present polypeptide

Ptac: tac promoter rrnBT1T2: terminator of ribosome RNA operon

AmpR: ampicillin resistant gene pBR322ori: replication initiation site of *Escherichia coli*

DETAILED DESCRIPTION OF THE INVENTION

The monoclonal antibody according to the present invention specifically reacts with a polypeptide having a specific amino acid sequence.

The hybridoma according to the present invention produces the monoclonal antibody when cultured in vitro.

The preparation of the monoclonal antibody according to the present invention facilitates its production in a desired amount.

The purification method of the polypeptide according to the present invention efficiently recovers it in a relatively-high quality from a mixture containing the polypeptide and impurities.

In the detection method according to the present invention, only the polypeptide in samples exhibits an immunological reaction. When the immunoreaction level is measured by an appropriate technique, the polypeptide can be qualitatively or quantitatively assayed.

Explaining now the present invention with reference to the Examples in the present specification, the monoclonal antibody according to the present invention includes those in general which are specific to the polypeptide having the amino acid sequence in SEQ ID NO:1 or homologous ones thereunto, independently of their source, origin or class. The homologous amino acids include those which are obtained by replacing one or more amino-acids in SEQ ID NO:1 with other amino acids, by adding one or more amino acids to the N- and/or C-termini in the amino acid sequence of SEQ ID NO:1, or by losing one or more amino acids in the N- and/or C-termini of the amino acid sequence in SEQ ID NO:1, while substantially not losing the activity of inducing IFN-γ production by immunocompetent cells.

The monoclonal antibody according to the present invention can be obtained by using the polypeptide or its antigenic fragments: For example, the antibody can be obtained by preparing hybridomas using mammalian cells capable of infinite proliferation and antibody-producing cells collected from mammals immunized with the fragments, selecting clones of hybridomas capable of producing the monoclonal antibody, and culturing the clones in vivo or in vitro.

The polypeptide as an antigen can be obtained by culturing transformants into which a DNA encoding the amino acid sequence in SEQ ID NO:1 and/or a homologous one was introduced, and, generally, they are used intact or in a partially purified form. The antigenic fragments can be prepared by chemically or enzymatically hydrolyzing the wholly or partially purified polypeptide, or synthesized by peptide synthesis based on the amino acid sequence in SEQ ID NO:1.

The immunization method usable in the present invention includes conventional ones: For example, antigens alone or in combination with adequate adjuvants are injected into mammals intravenously, intradermally, subcutaneously or intraperitoneally, and they are fed for a prescribed period. Any mammal can be used in the present invention without special restriction as long as desired antibody-producing cells can be obtained independently of the animal's species, weight and sex. In general, rodents such as rats, mice and hamsters are used, and from which the most suitable animal is selected while evaluating the compatibility with the above mammalian cells capable of infinite proliferation. Depending on the species and weight of animals used, the total dose of the antigens is generally in the range of about 5–500 µg per animal and administered 2–5 times at an interval of 1–2 weeks. On 3–5 days after the final administration, the animal's spleen is extracted and dispersed into a suspension of spleen cells as an antibody-producing cell.

The antibody-producing cells and the mammalian cells obtained in the above are fused into a cell fusion mixture containing the objective hybridomas. The mammalian cells capable of infinite proliferation include cell strains from mouse myeloma such as P3-NS1-Ag4-1 cells (ATCC TIB18), P3-X63-Ag8 cells (ATCC TIB9), SP2/0-Ag14 cells (ATCC CRL1581), and mutants thereof. The cell fusion method usable in the present invention includes conventional ones using an electric pulse and a cell fusion-accelerator such as polyethylene glycol and sendai virus (HVJ): For example, antibody-producing cells and such mammalian cells are suspended in fusion media containing fusion accelerators in a ratio of about 1:1 to 1:10, and incubated at about 30–40° C. for about 1–5 min. Conventional media such as minimum essential medium (MEM), RPMI 1640 medium, and Iscove's Modified Dulbecco's Medium (IMDM) are preferably used as a fusion medium without addition of serums such as calf serum.

To select the objective hybridomas, the resultant cell fusion mixture was transferred to selection media such as HAT medium, and incubated at about 30–40° C. for about 3 days to 3 weeks to kill cells except for the hybridomas. The hybridomas were cultured in the usual manner, and antibodies secreted in the cultures were assayed for reactivity with the polypeptide. Examples of such an assay are conventional ones for detecting antibodies such as an enzyme immunoassay, radioimmunoassay, and bioassay. For example, "*Tan-Clone-Kotai-Jikken-Manual* (Experimental Manual for Monoclonal Antibody)", edited by Sakuji TOYAMA and Tamie ANDO, published by Kodansha Scientific, Ltd., Tokyo, Japan, pp.105–152 (1991) describes a variety of them. Hybridomas, which produce antibodies that are specific to the polypeptide, are readily cloned by limiting dilution to obtain the hybridoma according to the present invention.

The monoclonal antibody according to the present invention can be obtained by culturing the hybridoma in vivo, i.e. in animals, or in vitro. For the culture conventional methods for culturing mammalian cells can be used: For example, in case of in vivo culture, the monoclonal antibody is collected from the animals' ascites and/or blood. The hybridomas H-1 and H-2 as described below have an enhanced producibility of the monoclonal antibody and have a character of being readily cultured in vivo and in vitro. Conventional methods used to purify antibodies in general can be used to collect the monoclonal antibody from the cultures, and animal's ascites and blood. Examples of such include salting out, dialysis, filtration, concentration, centrifugation, separatory sedimentation gel filtration chromatography, ion-exchange chromatography, affinity chromatography, high-performance liquid chromatography (HPLC), gel electrophoresis, and isoelectrophoresis, and, if necessary, two or more of these techniques can be used in combination. The resultant purified monoclonal antibodies can be concentrated or dried into products in the form of a liquid or a solid to meet to their final use.

The present monoclonal antibody is extremely useful for purifying the present polypeptide on immunoaffinity chromatography. Such a purification technique comprises contacting the monoclonal antibody with a mixture containing the polypeptide and impurities such as proteins except for the polypeptide to adsorb the polypeptide on the antibody, and desorbing the polypeptide from the antibody. These steps are generally carried out in an aqueous system. The monoclonal antibody is generally used in an immobilized form to gel water-insoluble carriers which are packed in cylindrical columns. Cultures of transformants or their partially purified products are fed to the columns to substantially adsorb the polypeptide on the monoclonal antibody. The polypeptide is readily desorbed from the antibody by alternating the pH around the antibody. For example, in the case of using a monoclonal antibody of the class IgG, the adsorbed polypeptide is desorbed and eluted from the columns at an acidic pH, usually, a pH of 2–3, while in the case of using a monoclonal antibody of the class IgM, the polypeptide is desorbed and eluted from the columns at an alkaline pH, usually, a pH of 10–11.

The purification method according to the present invention attains a relatively-high level purification of the polypeptide with only minimum labor cost and time. As is described above, the polypeptide has an activity of inducing IFN-γ production by immunocompetent cells, and the purified polypeptide can be used as an IFN-γ inducer for cell culture to produce IFN-γ, and used in the treatment and/or the prevention of virus diseases such as AIDS and condyloma, malignant tumors such as renal cancer, granuloma, mycosis fungoides, and cerebral tumor, and immune diseases such as articular rheumatism and allergy. If the polypeptide has an activity of enhancing the cell cytotoxicity of killer cells, it can be used together with interleukin 2 and/or tumor necrosis factor to improve the therapeutic effect and reduce the side effects in the treatment of adoptive immunity for malignant tumors including solid tumors such as lung cancer, renal cancer, and breast cancer.

The monoclonal antibody according to the present invention has a relatively-wide applicability to a variety of fields which require the detection of the polypeptide. When used in labelled immunoassays such as radioimmunoassay, enzyme immunoassay, and fluorescent immunoassay, the monoclonal antibody can qualitatively and quantitatively detect the polypeptide in samples instantly and accurately. In such assays, the monoclonal antibody is labelled, for example, with radioisotopes, enzymes and/or fluorescent substances prior to use. The antibody specifically reacts with the polypeptide to exhibit an immunoreaction, and accurately detects a slight amount of the polypeptide in samples by measuring the level of the immunoreaction for these labelled substances. As compared with bioassay, labelled immunoassay has the following features: It can assay many samples in parallel, reduce the assaying time and labor cost, and provide data with a relatively high in accuracy. Thus, the present detection method is useful for controlling the production steps of the polypeptide and for the quality control of the final products. Although the present invention does not describe in detail the techniques for labelling monoclonal antibody or labelling assay because it does not in itself relate to such an invention, these techniques are described in detail in "*Enzyme Immunoassay*", edited by P. Tijssen, translated by Eiji ISHIKAWA, published by Tokyo-Kagaku-Dojin, pp.196–348 (1989).

The following Examples explain the present invention, and can be variously modified by conventional methods in this art. In view of this, this invention should not be restricted to these Examples:

EXAMPLE 1

Preparation of Hybridoma H-1

EXAMPLE 1-1

Preparation of Transformant KGFHH2

To a 0.5-ml reaction tube were added 8 μl of 25 mM magnesium chloride, 10 μl of 10×PCR buffer, one μl of 25 mM dNTP mix, one μl of 2.5 units/μl of AmpliTaq DNA polymerase, one ng of a recombinant DNA containing the base sequence in SEQ ID NO:2 prepared from a phage DNA clone according to the method in Japanese Patent Application No.304,203/94 and containing a DNA encoding the polypeptide in SEQ ID NO:1, and an adequate amount of a sense primer and an anti-sense primer represented by 5'-ATAGAATTCAAATGTACTTTGGCAAGCTTGAATC-3' (SEQ ID NO:8), chemically synthesized based on an amino acid sequence near the N- and C-termini of SEQ ID NO:1, and 5'-ATAAAGCTTCTAGTCTTCGTTTTGAAC-3' (SEQ ID NO:9), and the mixture solution was volumed up with sterilized distilled water to give a total volume of 100 μl. The mixture solution was in the usual manner successively incubated at 94° C. for one min, at 43° C. for one min, and at 72° C. for one min, and this sequential incubation was repeated 3 times. The resultant mixture was further successively incubated at 94° C. for one min, at 60° C. for one min, and at 72° C. for one min, and this sequential incubation was repeated 40 times to effect PCR reaction.

The resultant PCR reaction mixture and "pCR-Script SK (+)", a plasmid vector commercialized by Stratagene Cloning Systems, California, USA, were ligated with DNA ligase to obtain a recombinant DNA which was then introduced with competent cell into "*Escherichia coil* XL-1 Blue MRF'Kan", a microorganism commercialized by Stratagene Cloning Systems, California, USA, to transform the microorganism. The transformant thus obtained was inoculated into L-broth (pH 7.2) containing 50 μg/ml ampicillin, and cultured at 37° C. for 18 hours under shaking conditions, followed by centrifuging the resultant culture to collect the proliferated transformants, and isolating recombinant DNAs with conventional alkaline-SDS method. A part of the recombinant DNAs was provided, analyzed by the on dideoxy method, and revealed that it contained a DNA which has cleavage sites of Eco RI and Hind III at the 5'- and 3'-termini of SEQ ID NO:2, a methionine codon which initiates the polypeptide synthesis and positions in the sites corresponding to the those before and after the N- and C-termini of SEQ ID NO:2, and a TAG codon which terminates the polypeptide synthesis.

Figure 1:
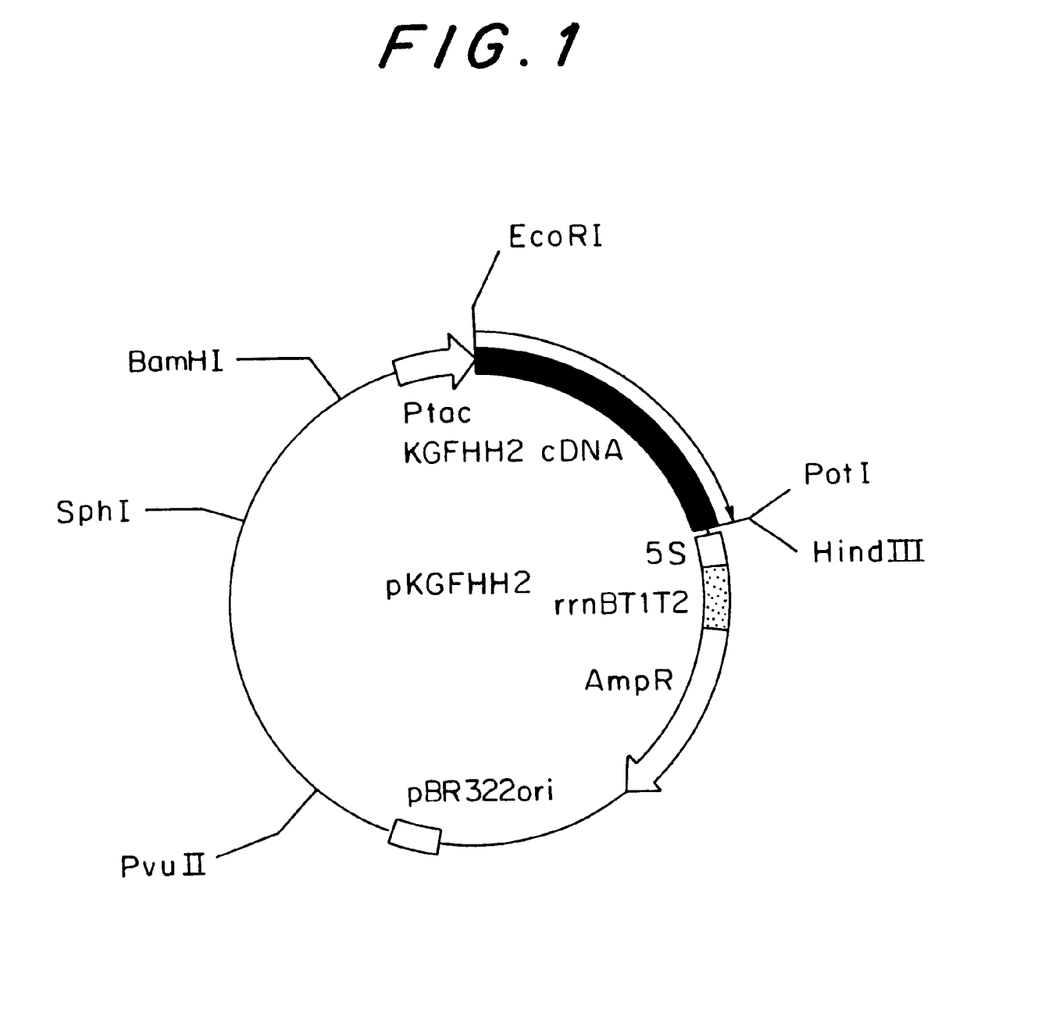
FIG. 1 is a figure of the structure of recombinant DNA pKGFHH2.

The remaining recombinant DNAs were cleaved with restriction enzymes Eco RI and Hind III, and 0.1 μg of the resultant Eco RI-Hind III DNA fragment obtained with "DNA LIGATION KIT Version 2", a DNA ligation kit commercialized by Takara Shuzo Co., Ltd., Tokyo, Japan, and 10 ng of "pKK223-3", a plasmid vector commercialized by Pharmacia LKB Biotechnology AB, Uppsala, Sweden, which had been previously cleaved with the above restriction enzymes, were ligated by incubating them at 16° C. for 30 min to obtain a replicable recombinant DNA "pKG-FHH2". By using the competent cell method, Escherichia coli Y1090 strain (ATCC 37197) was transformed with the replicable recombinant DNA pKGFHH2, and the formed transformant "KGFHH2" was inoculated into L-broth (pH 7.2) containing 50 µg/ml ampicillin, and incubated at 37° C. for 18 hours under shaking conditions. The resultant culture was centrifuged to collect the proliferated transformants, and a portion of this was treated by the conventional SDS-alkaline method to extract the recombinant DNA pKG-FHH2. As is shown in FIG. 1, the analysis of dideoxy method revealed that, in the recombinant DNA pKGFHH2, the KGFHH2 cDNA which contained the base sequence in SEQ ID NO:2 was ligated to the downstream of a Tac promoter.

EXAMPLE 1-2

Production of Polypeptide from Transformant KGFHH2

An L-broth (pH 7.2) containing 50 µg/ml of ampicillin was sterilized by autoclaving, cooled to 37° C., inoculated with the transformant KGFHH2 in Experiment 1-1, and incubated at the same temperature for 18 hours under shaking conditions to obtain a seed culture. An eighteen L quantity of a fresh preparation of the same medium was placed in a 20-L jar fermenter, sterilized similarly as above, cooled to 37° C., inoculated with one v/v % of the seed culture, and cultured at the same temperature for 8 hours under aeration and agitation conditions. The resultant culture was centrifuged to collect cells which were then suspended in a mixture solution (pH 7.3) consisting of 150 mM sodium chloride, 16 mM disodium hydrogen phosphate, and 4 mM sodium dihydrogen phosphate, disrupted with ultrasound, and centrifuged to remove cell debris to obtain a supernatant.

Ammonium sulfate was added to the supernatant to give a concentration of 40 w/v % and dissolved to homogeneity, and the solution was centrifuged to obtain a supernatant. The supernatant was first mixed with 150 mM phosphate buffer (pH 6.6) containing 1.5 M ammonium sulfate, then fed to a column packed with "PHENYL SEPHAROSE", a product of Pharmacia LKB Biotechnology AB, Uppsala, Sweden, which had been previously equilibrated with 10 mM phosphate buffer (pH 6.6) containing 1.5 M ammonium sulfate, followed by washing the column with a fresh preparation of the same buffer, and feeding to the column a gradient buffer of ammonium sulfate ranging from 1.5 M to 0 M in 10 mM phosphate buffer (pH 6.6).

Fractions eluted at around 1.0 M ammonium sulfate were pooled, membrane filtered, dialyzed against 10 mM phosphate buffer (pH 6.5) at 4° C. for 18 hours, and fed to a column packed with "DEAE 5PW", a product commercialized by Tosoh Corporation, Tokyo, Japan, which had been previously equilibrated with 10 mM phosphate buffer (pH 6.5), followed by washing the column with a fresh preparation of the same buffer, and feeding to the column a linear gradient buffer of sodium chloride ranging from 0 M to 0.2 M in 10 mM phosphate buffer (pH 6.5) while collecting fractions eluting at 0.05 M sodium chloride.

Thereafter, the fractions were concentrated with a membrane and fed to a column packed with "SUPER DEX 75", a product of Pharmacia LKB Biotechnology AB, Uppsala, Sweden, which had been equilibrated with phosphate buffered saline (hereinafter abbreviated as "PBS"), followed by feeding to the column a fresh preparation of PBS to collect fractions corresponding to about 18,500 daltons. Thus, an aqueous solution containing about 5.2 mg of a purified protein was obtained. The total yield throughout the purification was about 10%.

Analysis according to the method in Japanese Patent Application No.304,203/94 revealed that the purified protein had the following physicochemical properties: When electrophoresed in SDS-polyacrylamide gel under reducing conditions, the purified protein appeared as a main protein band having an IFN-γ inducibility at a position corresponding to 18,500±3,000 daltons, while giving a pI of 4.9±1.0 on chromatofocusing. The amino acid sequence containing N-terminus of the purified protein had the amino acid sequence in SEQ ID NO:3 equal to that in SEQ ID NO:1 where methionine was coupled to its N-terminus.

EXAMPLE 1-3

Preparation of Hybridoma H-1

BALB/c mice, 10-week-old, were intraperitoneally injected with 20 µg/mouse of a purified polypeptide, obtained by the method in Example 1-2, together with a complete Freund's adjuvant. The mice were further injected twice with the same dose at an interval of 2 weeks and intravenously injected with the same dose one week after the final injection, and their spleens were extracted and suspended to obtain a cell suspension.

The spleen cells and SP2/O-Ag14 cells from mouse myeloma (ATCC CRL 1581) were suspended in RPMI 1640 medium (pH 7.2) preheated to 37° C. at cell densities of $3 \times 10^4$ cells/ml and $1 \times 10^4$ cells/ml, respectively, and centrifuged to collect sediment. One ml of a serum-free RPMI 1640 medium (pH 7.2), containing 50 w/v % polyethylene glycol with an average molecular weight of 1,500 daltons, was added drop-wise to the sediment over a min, and the mixture was incubated at 37° C. for a min, followed by adding drop-wise to the mixture a serum-free RPMI 1640 medium (pH 7.2) up to give a total volume of 50 ml, centrifuging the mixture, and collecting the formed sediment. The sediment thus obtained was suspended in HAT medium, distributed to 96-well microplates in an amount of 200 µl/well, and incubated at 37° C. for one week, followed by selecting hybridomas.

The amount of antibodies secreted in the supernatant in each well was assayed on enzyme immunoassay based on the immunoreaction of the antibodies and a purified polypeptide, obtained by the method in Example 1-2, and hybridomas capable of producing antibodies, which strongly react with the purified polypeptide, were selected. A cloned hybridoma H-1 cell capable of producing the present monoclonal-antibody was in the usual manner obtained by repeatedly treating these hybridomas with limiting dilution.

EXAMPLE 2

Preparation of Monoclonal Antibody H-1mAb and Its Analysis On Western Blot Technique

EXAMPLE 2-1

Preparation of Monoclonal Antibody H-1mAb

Hybridoma H-1 cells obtained by the method in Example 1-3 were suspended in RPMI 1640 medium (pH 7.2) supplemented with 5 v/v % calf serum to give a cell density of about 1×10⁶ cells/ml, and incubated in an incubator at 37° C. under 5 v/v % $CO_2$ conditions while scaling up the culture. When the cell density of the culture reached a prescribed level, 1×10⁷ cells/mouse of the proliferated hybridoma H-1 cells were intraperitoneally injected into BALB/c mice, 8-week-old, which had been previously intraperitoneally injected with 0.5 ml/mouse of pristane, followed by feeding the mice in usual manner for one week.

From the mice ascites were collected, diluted with PBS by 3 times, mixed with ammonium sulfate to give a saturation degree of 50 w/v %, allowed to stand at 4° C. for 24 hours, and centrifuged to collect sediment. The sediment was dialyzed against an aqueous solution of 20 mM potassium dihydrogen phosphate (pH 6.7) at 4° C. overnight, and fed to a column of hydroxyapatite which had been previously equilibrated with a fresh preparation of the same aqueous solution, followed by feeding to the column a linear gradient potassium dihydrogen phosphate buffer (pH 6.7) ranging from 20 mM to 300 mM to obtain an aqueous solution containing the present monoclonal antibody H-1mAb. The yield was about 5 mg per mouse. Conventional analysis revealed that the antibody belongs to the class of $IgG_1$.

EXAMPLE 2-2

Analysis on Western Blot Technique

One µg of a purified polypeptide, obtained by the method in Example 1-2, was added to a mixture solution consisting of 100 mg dithiothreitol, 0.5 ml of an aqueous solution of 10 w/v % SDS, and one ml of glycerol, and the mixture was incubated at 37° C. for one hour and electrophoresed in SDS-polyacrylamide gel. The resultant gel was in usual manner transferred to a nitrocellulose membrane which was then soaked in a culture supernatant of hybridoma H-1 cells for one hour, and washed with 50 mM Tris-HCl buffer (pH 7.5) containing 0.05 v/v % TWEEN 20 to remove excessive amounts of antibodies. The membrane was further soaked for one hour in PBS containing an anti-mouse Ig antibody prepared from rabbits to effect immunoreaction, washed with 50 mM Tris-HCl buffer (pH 7.5) containing 0.05 v/v % TWEEN 20, and soaked in 50 mM Tris-HCl buffer (pH 7.5) containing 0.005 v/v % hydrogen peroxide and 0.3 mg/ml 3,3'-diaminobenzidine to effect coloration.

As a control, a system using a recombinant human interleukin 12 in place of the purified polypeptide was provided, and similarly treated as above. Calf serum albumin (MW=67,000 daltons), ovalbumin (MW=45,000 daltons), carbonic anhydrase (MW=30,000 daltons), trypsin inhibitor (MW=20,100 daltons), and α-lactalbumin (MW=14,400 daltons) were used as a marker protein. These results are shown in FIG. 2.

Figure 2:
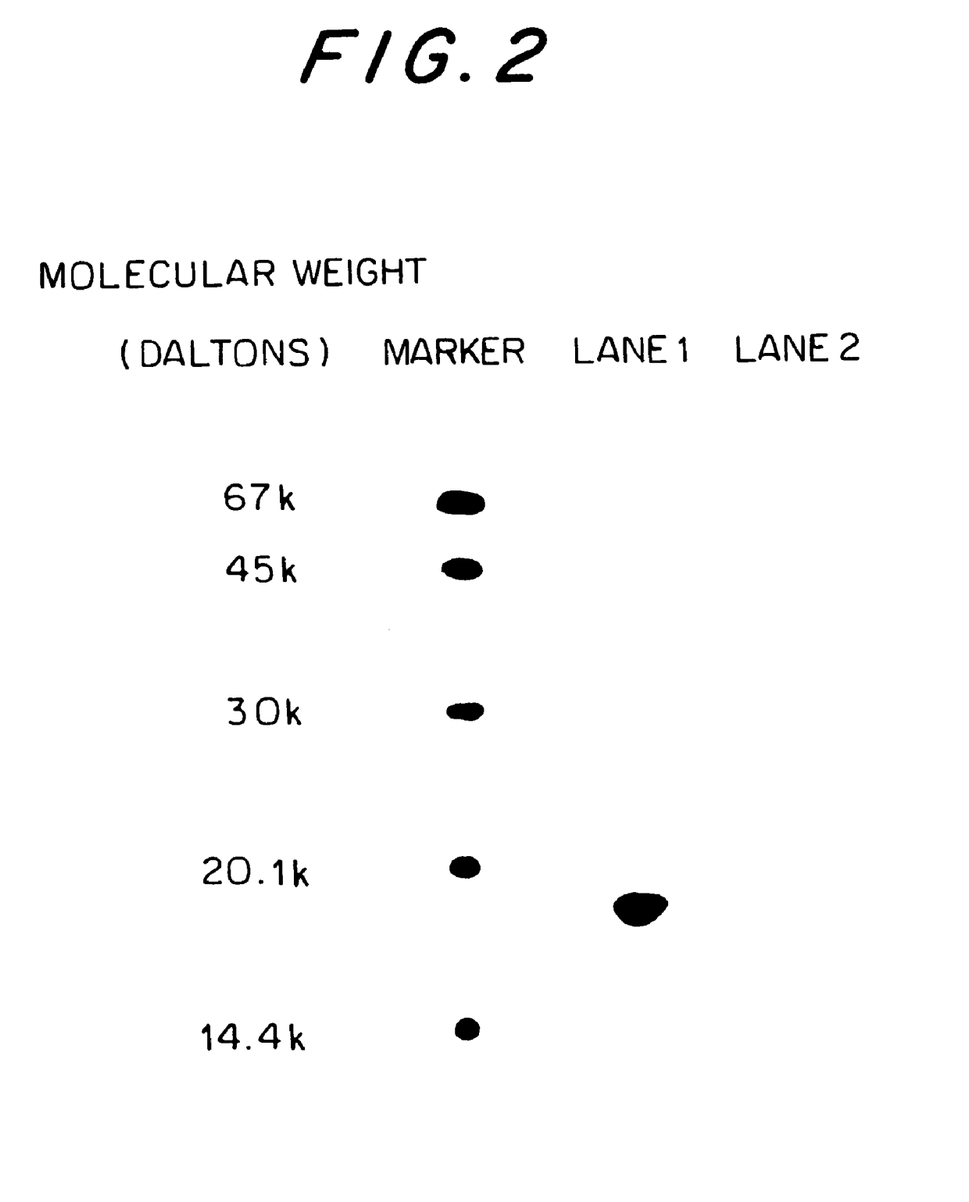
FIG. 2 is a figure of the Western blotting which shows the reactivity of the present purified polypeptide and human interleukin 12 with the present monoclonal antibody H-1mAb.

As is evident from FIG. 2, the monoclonal antibody H-1mAb specifically reacted with the purified polypeptide (lane 1) obtained by the method in Example 1, but did not react with the human interleukin 12 (lane 2). This demonstrates that the present monoclonal antibody specifically reacts with a polypeptide with a specific amino acid sequence.

EXAMPLE 3

Preparation of Hybridoma H-2 and Monoclonal Antibody H-2mAb

Hybridoma H-2, a monoclonal antibody, was similarly prepared by the method in Example 2-1 except that P3-X63-Ag8 cells (ATCC TIB9) were used in place of the SP/O-14Ag cells.

EXAMPLE 3-2

Preparation of Monoclonal Antibody H-2mAb

The hybridoma H-2 in Example 3-1 was cultured similarly as in Example 2-1, and the culture was purified to obtain about 5.6 mg of monoclonal antibody H-2mAb per BALB/c mouse. Conventional analysis revealed that the monoclonal antibody belongs to the class of IgM, and it specifically reacted with a purified polypeptide obtained by the method in Example 1-2 when analyzed on Western blotting technique similarly as in Example 2-2.

EXAMPLE 4

Purification of Polypeptide on Immunoaffinity Chromatography

EXAMPLE 4-1

Preparation of Gel for Immunoaffinity Chromatography

Eighty mg of monoclonal antibody H-1mAb, obtained by the method in Example 2-1, was weighed and dialyzed against 0.1 M borate buffer (pH 8.5) containing 0.5 M sodium chloride at 4° C. overnight. Four g of "CNBr-activated Sepharose 4B", a water-insoluble carrier commercialized by Pharmacia LKB Biotechnology AB, Uppsala, Sweden, was swollen with one mM of aqueous chloric acid solution, successively washed with a fresh preparation of the same buffer and 0.1 M borate buffer (pH 8.5) containing 0.5 M sodium chloride, admixed with an about 10 ml of the aqueous monoclonal antibody solution obtained in the above, and successively incubated at ambient temperature and at 4° C. overnight under gentle stirring conditions. Thereafter, the resultant gel was successively washed with one M aqueous ethanol amine solution (pH 8.0), 0.1 M borate buffer (pH 8.5) containing 0.5 M sodium chloride, and 0.1 M acetate buffer (pH 4.0), and these washing steps were repeated 5 times. Finally, the gel was washed with PBS to obtain a gel for immunoaffinity chromatography. Conventional analysis revealed that about 6 mg monoclonal antibody H-1mAb linked to one ml of the gel.

EXAMPLE 4-2

Purification of Polypeptide by Immunoaffinity Chromatography

Ten ml of the gel for immunoaffinity chromatography in Example 4-1 was packed in a plastic cylindrical column, washed with PBS, and fed with 10 ml of a Phenyl Sepharose eluted fraction containing about 0.1 mg/ml of the polypeptide obtained by the method in Example 1-2. The column was washed with a fresh preparation of PBS, and fed with 0.1 M glycine-HCl buffer (pH 2.5) containing one M sodium chloride to collect fractions with an IFN-γ inducing activity. The fractions were pooled, dialyzed against PBS at 4° C. overnight, concentrated and assayed for the IFN-γ inducing activity and the protein content, revealing that this purification procedure yielded a purified polypeptide with a purity of 95 w/w % or higher in a yield of about 100%.

EXAMPLE 5

Detection of Polypeptide on Enzyme Immunoassay

Rabbits were in the usual manner immunized with a purified polypeptide obtained by the method in Example 1-2, and their blood was collected. Immunoglobulin G antibody was isolated from the blood, dissolved in PBS to give a concentration of 20 µg/ml, and the solution was distributed into 96-well microplates in an amount of 100 µl/well. The microplates were incubated at ambient temperature for 3 hours, followed by removing solutions containing IgG from the microplates, adding PBS containing one w/v % calf serum albumin to the microplates in an amount of 200 µl/well, and allowing them to stand at 4° C. overnight.

Phosphate buffered saline was removed from the microplates which were then washed with PBS containing 0.05 v/v % TWEEN 20; and injected with 100 µl/well of a solution prepared by appropriately diluting a purified polypeptide, obtained by the method in Example 1-2, with PBS containing 0.5 w/v % calf serum albumin, followed by reacting the mixture solution at ambient temperature for 2 hours under shaking conditions. The microplates were washed with PBS containing 0.05 v/v % TWEEN 20, and injected with 100 µl/well of a solution containing a monoclonal antibody H-1mAb labelled with biotin, followed by reacting the mixture solution at ambient temperature for 2 hours under shaking conditions, washing the microplates with PBS containing 0.05 v/v % TWEEN 20, injecting with 100 µl/well of a solution containing a complex of horseradish peroxidase and streptoavidin, and further reacting the resultant mixture at ambient temperature for 2 hours under shaking conditions. Then, the microplates were washed with PBS containing 0.05 v/v % TWEEN 20, and the activity of the horseradish peroxidase linked to the purified polypeptide was measured for absorbance at a wavelength of 492 nm using o-phenylenediamine as a substrate. The results are shown in Table 1.

TABLE 1

| Concentration of polypeptide (pg/ml) | Absorbance at 492 nm* | Relative error (%) |
|---|---|---|
| 1,000 | 1.51 ± 0.05 | 3.3 |
| 500 | 0.93 ± 0.05 | 5.4 |
| 250 | 0.55 ± 0.03 | 5.5 |
| 100 | 0.25 ± 0.02 | 8.0 |
| 50 | 0.137 ± 0.007 | 5.1 |
| 25 | 0.080 ± 0.007 | 8.8 |
| 0 | 0.024 ± 0.007 | — |

Note: The symbol "*" means a statistical value of triplet.

As is evident from the results in Table 1, the detection method according to the present invention accurately assays the polypeptide in the range of about 50–1,000 pg/ml.

EXAMPLE 6

Detection of Polypeptide on Radioimmunoassay

Rabbits were immunized in the usual manner with a purified polypeptide obtained by the method in Example 1-2, and their blood collected, followed by isolating IgG antibody. The antibody was absorbed in the usual manner on polystyrene beads for radioimmunoassay, and allowed to stand in PBS containing 2 w/v % calf serum albumin at 4° C. overnight to obtain an immobilized antibody.

One bead was placed in a test tube, soaked in 0.2 ml of a solution prepared by diluting a purified polypeptide, obtained by the method in Example 1-2, with PBS containing 0.5 w/v % calf serum albumin, and allowed to stand at 4° C. for 4 hours. Then, the bead was washed with PBS containing 0.05 v/v % TWEEN 20 and 0.5 w/v % calf serum albumin, soaked in 0.2 ml ($1 \times 10^5$ cpm) of a solution containing a monoclonal antibody H-2mAb, obtained by the method in Example 3-2 and labelled with $^{125}I$, and allowed to stand at 4° C. overnight. After removing an excessive amount of $^{125}I$-labelled antibody, the bead was washed with PBS containing 0.05 v/v % TWEEN 20 and 0.5 w/v % calf serum albumin, followed by counting the radioactivity of the bead on a gamma-counter. The results were in Table 2.

TABLE 2

| Concentration of polypeptide (pg/ml) | Count* (cpm) | Relative error (%) |
|---|---|---|
| 1,000.0 | 6900 ± 200 | 2.9 |
| 500.0 | 4100 ± 20 | 0.5 |
| 250.0 | 2390 ± 50 | 2.1 |
| 125.0 | 1590 ± 70 | 4.4 |
| 62.5 | 880 ± 10 | 1.1 |
| 0 | 700 ± 20 | — |

Note: The symbol "*" means a statistical value of triplet.

As is evident from the results in Table 2, the present detection method accurately assays the polypeptide in the range of about 100–1,000 pg/ml.

As is described above, the present monoclonal antibody specifically reacts with a polypeptide which induces IFN-γ production by immunocompetent cells. Therefore, the monoclonal antibody is widely used in the purification and detection of the polypeptide, and is prepared in a desired amount by a preparation using hybridomas.

The present invention with these significant functions and effects is a significant invention which greatly contributes to this field.

While there has been described what is at present considered to be the preferred embodiments of the invention, it will be understood that various modifications may be made therein, and it is intended to cover in the appended claims all such modifications as fall within the true spirit and scope of the invention.

We claim:

1. A monoclonal antibody which specifically binds to a polypeptide with an amino acid sequence of SEQ ID NO:1, where Xaa represents isoleucine or threonine, which polypeptide induces human IFN-γ production by immunocompetent cells and has a molecular weight of 18,500±3,000 daltons on SDS-PAGE and a pI of 4.9±1.0 on chromatofocusing.

2. The monoclonal antibody of claim 1, which belongs to the class of IgG or IgM.

3. A composition for neutralizing a polypeptide, which comprises the monoclonal antibody of claim 1 as an effective ingredient and a carrier of the monoclonal antibody.

4. A process for preparing the monoclonal antibody of claim 1, comprising the steps of:

culturing a hybridoma to produce the monoclonal antibody in a nutrient culture medium; and collecting and purifying the produced monoclonal antibody from the resultant nutrient culture medium, wherein said hybridoma is obtained by:

(a) immunizing an animal with a fragment of a polypeptide of SEQ ID NO:1 or a whole molecule of a polypeptide of SEQ ID NO:1, where Xaa represents isoleucine or threonine;

(b) collecting an antibody-producing cell from the immunized animal;

(c) fusing the antibody-producing cell with a mammalian cell capable of infinite proliferation to form a hybridoma; and (d) selecting a clone of the hybridoma which produces the monoclonal antibody which binds to the polypeptide.

5. The process of claim 4, wherein said monoclonal antibody in purified from the nutrient culture medium by at least one technique selected from the group consisting of salting out, dialysis, filtration, concentration, centrifugation, separatory sedimentation, gel filtration chromatography, ion-exchange chromatography, affinity chromatography, gel electrophoresis, and isoelectrophoresis.

6. A hybridoma capable of producing the monoclonal antibody of claim 1.

* * * * *